US009827367B2

(12) United States Patent
Perry et al.

(10) Patent No.: US 9,827,367 B2
(45) Date of Patent: Nov. 28, 2017

(54) SURGICAL INSTRUMENT, SYSTEM, AND METHOD FOR FRONTAL SINUS IRRIGATION

(75) Inventors: Isaac C. Perry, Jacksonville, FL (US); John R. Prisco, Jacksonville, FL (US); Dale E. Slenker, Jacksonville, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 1259 days.

(21) Appl. No.: 12/111,804

(22) Filed: Apr. 29, 2008

(65) Prior Publication Data

US 2009/0270796 A1 Oct. 29, 2009

(51) Int. Cl.
*A61M 3/02* (2006.01)
*A61M 31/00* (2006.01)
*A61B 1/233* (2006.01)

(52) U.S. Cl.
CPC .......... *A61M 3/0279* (2013.01); *A61M 3/025* (2013.01); *A61M 3/0216* (2014.02);
(Continued)

(58) Field of Classification Search
CPC .............. A61M 3/0216; A61M 3/0254; A61M 3/0258; A61M 3/0275; A61M 3/0279; A61M 2206/16; A61M 2210/0618; A61M 2210/0681; A61M 3/02; A61M 3/0204; A61M 3/0233; A61M 3/025; A61M 31/00; A61M 37/00; A61M 37/0092
(Continued)

(56) References Cited

U.S. PATENT DOCUMENTS 1,487,252 A 3/1924 Lore
1,843,169 A 2/1932 McKesson
(Continued)

FOREIGN PATENT DOCUMENTS

JP 09-084800 3/1997
JP 2002-543868 11/2000
(Continued)

OTHER PUBLICATIONS

Y. Zhang et al., "Detection of *Streptococcus pneumoniae* in Whole Blood by PCR," Journal of Clinical Microbiology, Mar. 1995, pp. 596-601.
(Continued)

*Primary Examiner* — Shefali Patel
(74) *Attorney, Agent, or Firm* — Dicke, Billig & Czaja, PLLC

(57) ABSTRACT

A surgical instrument for irrigating a frontal sinus target site of a patient including a handle, an introducer, an irrigation channel, a nozzle, and an actuator assembly. The introducer extends from the handle and defines a proximal segment and a distal segment. At least a portion of the proximal segment is linear and at least a portion of the distal segment is relatively curved. The nozzle is fluidly connected to the irrigation channel, and is rotatably maintained at a distal end of the introducer. The actuator assembly includes an actuator maintained by the handle and connected to the nozzle. Movement of the actuator causes the nozzle to rotate relative to the introducer. The introducer can be sized and shaped in accordance with a size and a shape of a nasal passageway/frontal sinus of a human adult.

20 Claims, 5 Drawing Sheets

(52) U.S. Cl.
CPC ........ *A61M 3/0233* (2013.01); *A61M 3/0258* (2013.01); *A61M 31/00* (2013.01); *A61B 1/233* (2013.01); *A61M 2206/16* (2013.01); *A61M 2210/0618* (2013.01); *A61M 2210/0681* (2013.01)

(58) Field of Classification Search
USPC ..... 604/131, 151, 164.04, 170.03, 264, 275, 604/500, 514, 95.01
See application file for complete search history.

(56) References Cited

U.S. PATENT DOCUMENTS

| | | | |
|---|---|---|---|
| 1,987,907 A | 1/1935 | Jenkins | |
| 2,243,299 A | 5/1941 | Travers | |
| 2,280,992 A | 4/1942 | Wright et al. | |
| 2,812,765 A | 11/1957 | Tofflemire | |
| 3,208,145 A | 9/1965 | Turner | |
| 3,452,745 A * | 7/1969 | Spitz ................... | A61C 17/028 601/161 |
| 3,470,876 A | 10/1969 | Barchilon | |
| 3,749,090 A | 7/1973 | Stewart | |
| 3,980,078 A | 9/1976 | Tominaga | |
| 4,282,867 A * | 8/1981 | Du Toit .............. | A61M 3/0258 601/161 |
| 4,299,221 A | 11/1981 | Phillips et al. | |
| 4,397,640 A | 8/1983 | Haug et al. | |
| 4,408,598 A | 10/1983 | Ueda | |
| 4,487,600 A | 12/1984 | Brownlie et al. | |
| 4,517,962 A | 5/1985 | Heckele | |
| 4,519,385 A | 5/1985 | Atkinson et al. | |
| 4,526,573 A | 7/1985 | Lester et al. | |
| 4,573,979 A | 3/1986 | Blake | |
| 4,583,531 A | 4/1986 | Mattchen | |
| 4,604,089 A | 8/1986 | Santangelo et al. | |
| 4,617,013 A | 10/1986 | Betz | |
| 4,680,026 A | 7/1987 | Weightman et al. | |
| 4,696,669 A | 9/1987 | Menhusen | |
| 4,708,717 A | 11/1987 | Deane et al. | |
| 4,776,840 A | 10/1988 | Freitas et al. | |
| 4,801,292 A | 1/1989 | Watson | |
| 4,881,523 A | 11/1989 | Heckele | |
| 4,911,148 A | 3/1990 | Sosnowski et al. | |
| 4,941,872 A | 7/1990 | Felix et al. | |
| 4,964,849 A | 10/1990 | Robicsek | |
| 4,979,497 A | 12/1990 | Matsura et al. | |
| 4,991,565 A | 2/1991 | Takahashi et al. | |
| 5,100,377 A | 3/1992 | Freitas et al. | |
| 5,147,292 A | 9/1992 | Kullas et al. | |
| 5,170,774 A | 12/1992 | Heckele | |
| 5,199,950 A | 4/1993 | Schmitt et al. | |
| 5,201,908 A | 4/1993 | Jones | |
| 5,203,769 A | 4/1993 | Clement et al. | |
| 5,224,929 A | 7/1993 | Remiszewski | |
| 5,230,704 A | 7/1993 | Moberg et al. | |
| 5,231,989 A | 8/1993 | Middleman et al. | |
| 5,286,253 A | 2/1994 | Fucci | |
| 5,295,956 A | 3/1994 | Bales et al. | |
| 5,312,327 A | 5/1994 | Bales et al. | |
| 5,314,406 A | 5/1994 | Arias et al. | |
| 5,318,526 A | 6/1994 | Cohen | |
| 5,322,503 A | 6/1994 | Desai | |
| 5,325,845 A | 7/1994 | Adair | |
| 5,328,467 A | 7/1994 | Edwards et al. | |
| 5,342,299 A | 8/1994 | Snoke et al. | |
| 5,354,267 A | 10/1994 | Niermann et al. | |
| 5,372,587 A | 12/1994 | Hammerslag et al. | |
| 5,378,234 A | 1/1995 | Hammerslag et al. | |
| 5,383,852 A | 1/1995 | Stevens-Wright | |
| 5,386,817 A | 2/1995 | Jones | |
| 5,397,321 A | 3/1995 | Houser et al. | |
| 5,429,596 A | 7/1995 | Arias et al. | |
| 5,437,636 A | 8/1995 | Snoke et al. | |
| 5,443,445 A | 8/1995 | Peters et al. | |
| 5,462,527 A | 10/1995 | Stevens-Wright et al. | |
| 5,484,402 A | 1/1996 | Saravia et al. | |
| 5,496,314 A | 3/1996 | Eggers | |
| 5,520,222 A | 5/1996 | Chikama | |
| 5,554,112 A | 9/1996 | Walbrink et al. | |
| 5,575,752 A | 11/1996 | Yabe et al. | |
| 5,575,756 A | 11/1996 | Karasawa et al. | |
| 5,607,391 A | 3/1997 | Klinger et al. | |
| 5,609,573 A | 3/1997 | Sandock | |
| 5,709,698 A | 1/1998 | Adams et al. | |
| 5,792,098 A | 8/1998 | Felix et al. | |
| 5,842,973 A | 12/1998 | Bullard | |
| 5,855,549 A | 1/1999 | Newman | |
| 5,928,191 A | 7/1999 | Houser et al. | |
| 5,944,689 A | 8/1999 | Houser et al. | |
| 5,989,183 A | 11/1999 | Reisdorf et al. | |
| 5,993,410 A | 11/1999 | Vincent et al. | |
| 6,030,360 A | 2/2000 | Biggs | |
| 6,086,542 A | 7/2000 | Glowa et al. | |
| 6,110,103 A | 8/2000 | Donofrio | |
| 6,126,633 A | 10/2000 | Kaji et al. | |
| 6,174,280 B1 | 1/2001 | Oneda et al. | |
| 6,179,776 B1 | 1/2001 | Adams et al. | |
| 6,282,442 B1 | 8/2001 | DeStefano et al. | |
| 6,293,957 B1 | 9/2001 | Peters et al. | |
| 6,364,853 B1 | 4/2002 | French et al. | |
| 6,551,302 B1 | 4/2003 | Rosinko et al. | |
| 6,599,237 B1 | 7/2003 | Singh | |
| 6,623,445 B1 | 9/2003 | Nelson et al. | |
| 6,652,488 B1 | 11/2003 | Cover et al. | |
| 6,679,834 B2 | 1/2004 | Stahl et al. | |
| 6,712,757 B2 | 3/2004 | Becker et al. | |
| 6,712,759 B2 | 3/2004 | Muller | |
| 6,746,419 B1 | 6/2004 | Arnett et al. | |
| 6,770,050 B2 | 8/2004 | Epstein | |
| 6,811,544 B2 | 11/2004 | Schaer | |
| 6,863,668 B2 | 3/2005 | Gillespie et al. | |
| 6,907,879 B2 | 6/2005 | Drinan et al. | |
| 6,918,902 B2 | 7/2005 | French et al. | |
| 6,939,293 B2 | 9/2005 | Conteas | |
| 6,945,956 B2 | 9/2005 | Waldhauser et al. | |
| 7,025,759 B2 | 4/2006 | Muller | |
| 7,144,383 B2 | 12/2006 | Arnett et al. | |
| 2001/0025134 A1 | 9/2001 | Bon et al. | |
| 2003/0176769 A1 | 9/2003 | Soble et al. | |
| 2003/0181934 A1 | 9/2003 | Johnston et al. | |
| 2004/0059191 A1 | 3/2004 | Krupa et al. | |
| 2004/0202670 A1* | 10/2004 | Apicella ............. | C07K 14/285 424/184.1 |
| 2004/0267213 A1 | 12/2004 | Knapp | |
| 2005/0075621 A1 | 4/2005 | Rontal | |
| 2005/0080396 A1 | 4/2005 | Rontal | |
| 2005/0107853 A1 | 5/2005 | Krespi et al. | |
| 2005/0182353 A1 | 8/2005 | Schmidberger et al. | |
| 2005/0240147 A1 | 10/2005 | Makower et al. | |
| 2006/0004286 A1 | 1/2006 | Chang et al. | |
| 2006/0004323 A1 | 1/2006 | Chang et al. | |
| 2006/0009678 A1 | 1/2006 | Jaffe et al. | |
| 2006/0015009 A1 | 1/2006 | Jaffe et al. | |
| 2006/0015010 A1 | 1/2006 | Jaffe et al. | |
| 2006/0025652 A1 | 2/2006 | Vargas | |
| 2006/0041186 A1 | 2/2006 | Vancaillie | |
| 2006/0063973 A1 | 3/2006 | Makower et al. | |
| 2006/0069343 A1* | 3/2006 | Rontal .................. | A61B 17/22 604/20 |
| 2006/0084910 A1 | 4/2006 | Hoffman | |
| 2006/0095066 A1 | 5/2006 | Chang et al. | |
| 2006/0100481 A1 | 5/2006 | Soble et al. | |
| 2006/0111615 A1 | 5/2006 | Danitz et al. | |
| 2006/0210605 A1 | 9/2006 | Chang et al. | |
| 2006/0224103 A1 | 10/2006 | Rontal | |
| 2007/0250105 A1* | 10/2007 | Ressemann ...... | A61B 17/12022 606/196 |
| 2007/0264296 A1 | 11/2007 | Myntti | |
| 2007/0264342 A1* | 11/2007 | Oliver ................. | A61K 9/0043 424/486 |

(56) References Cited

U.S. PATENT DOCUMENTS

2008/0214891 A1* 9/2008 Slenker et al. ............... 600/109
2008/0249483 A1 10/2008 Slenker et al.

FOREIGN PATENT DOCUMENTS

| KR | 0289606 Y1 | 9/2002 |
|----|------------|--------|
| KR | 0439992 B1 | 7/2004 |
| WO | 00/67647 A1 | 11/2000 |
| WO | 2004006788 A1 | 1/2004 |
| WO | 2008/106298 A1 | 9/2008 |
| WO | 2008/124376 A1 | 10/2008 |

OTHER PUBLICATIONS

J. Christopher Post, MD et al., "Molecular Analysis of Bacterial Pathogens in Otitis Media with Effusion," JAMA, May 24-31, 1995, vol. 273, No. 20; 7 pgs.

E. M. Liederman, MD et al., "Analysis of Adult Otitis Media: Polymerase Chain Reaction Versus Culture for Bacteria and Viruses," Ann Otol Rhinol Laryngol 107:1998; pp. 10-16.

J. J. Aul, MD et al., "Comparative Evaluation and Culture and PCR for the Detection and Determination of Persistence of Bacterial Strains and DNAs in the Chinchilla Laniger Model of Otitis Media," Ann Otol Rhinol Laryngol 107:1998; pp. 508-513.

L. O. Bakaletz et al., "Blinded Multiplex PCR Analyses of Middle Ear and Nasopharyngeal Fluids from Chinchilla Models of Single- and Mixed-Pathogen-Induced Otitis Media," Clinical and Diagnostic Laboratory Immunology, Mar. 1998, pp. 219-224.

J.R. Dingman et al., "Correlation Between Presence of Viable Bacteria and Presence of Endotoxin in Middle-Ear Effusions," Journal of Clinical Microbiology, Nov. 1998, pp. 3417-3419.

J.W. Costerton, "Introduction to Biofilm," International Journal of Antimicrobial Agents 11 (1999); Dec. 2001; pp. 217-221.

J. Christopher Post, MD, PhD, "Direct Evidence of Bacterial Biofilms in Otitis Media," The Laryngoscope, Dec. 2001; pp. 2083-2094.

J.W. Costerson et al., "Battling Iofilms," Scientific American, Jul. 2001; pp. 75-81.

P.S. Mason et al., "Effect of Bacterial Endotoxin and Middle Ear Effusion on Ciliary Activity: Implications for Otitis Media," The Laryngoscope; Apr. 2002; pp. 676-680.

G.D. Ehrlich, PhD et al., "Mucosal Biofilm Formation on Middle-Ear Mucosa in the Chinchilla Model of Otitis Media," JAMA, Apr. 3, 2002, vol. 287, No. 13; pp. 1710-1715.

R.M. Donlan et al., "Biofilms: Survival Mechanisms of Clinically Relevant Microorganisms," Clinical Microbiology Reviews, Apr. 2002, pp. 167-193.

J. Cryer et al., "Evidence of Bactrial Biofilms in Human Chronic Sinusitis," Department of Otorhinolaryngology—Head and Neck Surgery, University of Pennsylvania Medical Center; 2004; pp. 155-158.

G.T. Rodeheaver, PhD, "Wound Cleansing, Wound Irrigation, Wound Disinfection," Chronic Wound Care: A Clinical Source Book for Healthcare Professionals, Third Edition, 2001; pp. 369-383.

J.N. Palmer MD, "Bacterial Biofilms: Do They Play a Role in Chronic Sinusitis?" Department of Otolaryngology—Head and Neck Surgery, Hospital of Pennsylvania, 2005; pp. 1193-1201.

A.Tripathi, MD et al., "Staphylococcal Exotoxins and Nasal Polyposis: Analysis of Systemic and Local Responses," American Journal of Rhinology, Jul.-Aug. 2005, vol. 19, No. 4; pp. 327-333.

J.E. Dohar, MD, MS et al., "Mucosal Biofilm Formation on Middle-Ear Mucosa in a Nonhuman Primate Model of Chronic Suppurative Otitis Media," The Laryngoscope, Aug. 2005; pp. 1469-1472.

B.J. Ferguson MD et al., "Demonstration of Biofilm in Human Bacterial Chronic Rhinosinusitis," American Journal of Rhinology, Sep.-Oct. 2005, vol. 19, No. 5, pp. 452-457.

L. Hall-Stoodley, PhD et al, "Direct Detection of Bacterial Biofilms on the Middle-Ear Mucosa of Children with Chronic Otitis Media," JAMA, Jul. 12, 2006, vol. 296, No. 2, pp. 202-211.

Z. Bendouah, BSC et al., "Biofilm Formation by *Staphylococcus aureus* and *Pseudomonas aeruginosa* is Associated with an Unfavorable Evolution After Surgery for Chronic Sinusitis and Nasal Polyposis," American Academy of Otolaryngology—Head and Neck Surgery Foundation; 2006; pp. 991-996.

U.S. Appl. No. 11/621,453, filed Jan. 9, 2007.

U.S. Appl. No. 11/680,781, filed Mar. 1, 2007.

PCT Search Report for PCT/US2008/058971, dated Aug. 20, 2008, 12 pgs.

* cited by examiner

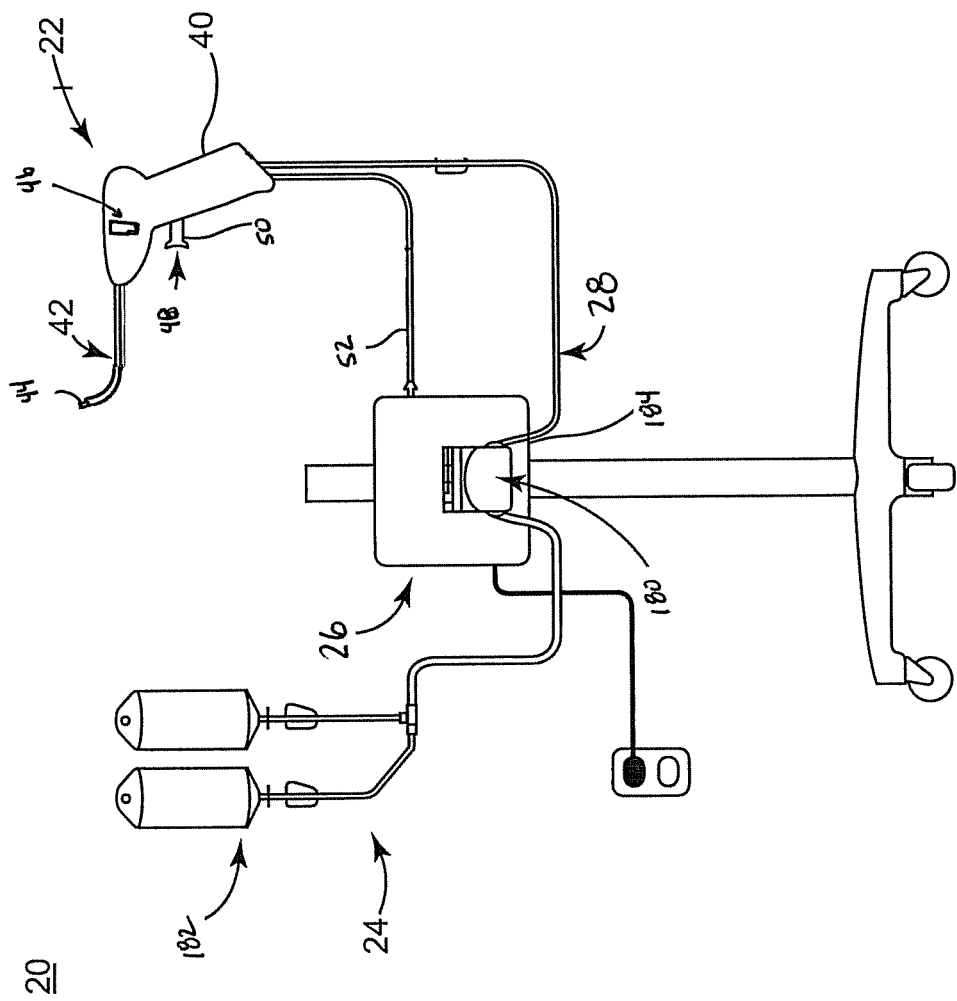

SURGICAL INSTRUMENT, SYSTEM, AND METHOD FOR FRONTAL SINUS IRRIGATION

CROSS-REFERENCE TO RELATED APPLICATION

This application is related to U.S. patent application Ser. No. 11/697,789 filed Apr. 9, 2007 and entitled "Surgical Instrument, System, and Method for Biofilm Removal," the entire teachings of which are incorporated herein by reference.

BACKGROUND

The present disclosure relates to systems and methods for delivering an irrigant to the frontal sinus of a patient. More particularly, it relates to systems and methods for surgically treating the frontal sinuses, for example in removing bacterial biofilms.

Bacterial biofilms develop in a variety of bodily cavities, including those of the ear, such as the middle ear, and those of the nose, such as the frontal or maxillary sinuses, for example. Once bacterial growth has been established, the bacteria will often aggregate, stop dividing, and begin forming protective bacterial biofilm layers, or "slime layers," comprised of polysaccharide matrices.

The protective bacterial biofilm interferes with the body's natural immune response as well as traditional methods of treatment. In particular, the bacteria emit exotoxins, which incite the body's immune system to respond with white cells. However, the bacterial biofilm interferes with the efficacy of the white cells' ability to attack the bacteria. The biofilm can also act as a barrier against topically administered antibiotics and other medicaments. Biofilm-forming bacteria also present obstacles to traditional, antibiotic treatments that act to kill dividing bacteria. In particular, the bacteria in a biofilm-forming state may have already ceased cell division, rendering such antibiotics largely ineffective.

Functional endoscopic sinus surgery (FESS) is a minimally invasive surgical procedure used to treat chronic rhinosinusitis, and possibly other infections of the sinuses. FESS opens up sinus air cells and sinus ostia (openings) with an instrument aided by an endoscope. The use of FESS as a sinus surgical method has now become widely accepted. The purpose of FESS is typically to restore normal drainage of the sinuses and to allow their ventilation. However, FESS does not address the bacterial biofilm concerns described above.

While ventilation surgery may incidentally cause some biofilms to slough off, many remain after surgery and it has been postulated that further therapies are required to remove bacterial biofilms in the paranasal sinuses and other bodily locations. In this regard, systems have been contemplated that act to destroy bacterial biofilm via delivery of a pressurized irrigant. Examples of such systems are described in commonly-assigned U.S. patent application Ser. No. 11/697,789. With these, as well as other sinus irrigation procedures unrelated to biofilm removal, certain target sites present anatomical barriers that may impede use of various instruments.

SUMMARY

Some aspects in accordance with principles of the present disclosure relate to a surgical instrument for irrigating a frontal sinus target site of a patient. The instrument includes a handle, an elongate introducer, an irrigation channel, a nozzle, and an actuator assembly. The introducer rigidly extends from the handle and defines a proximal segment and a distal segment terminating at a distal end. At least a portion of the proximal segment is relatively linear, and at least a portion of the distal segment is relatively curved. More particularly, in terms of longitudinal extension of the introducer from the handle, the curved portion of the distal segment is more curved as compared to the relatively linear portion of the proximal segment. The irrigation channel extends through the introducer. The nozzle is fluidly connected to the irrigation channel, and is maintained at the distal end of the introducer. In this regard, the nozzle is rotatable relative to the introducer. Finally, the actuator assembly includes an actuator maintained by the handle and connected to the nozzle. With this configuration, movement of the actuator causes the nozzle to rotate relative to the introducer. In some embodiments, the introducer is sized and shaped in accordance with a size and shape of the nasal/frontal sinus passageway of a human adult. In other embodiments, the instrument further includes an irrigation assembly rotatably disposed within the introducer, with the irrigation assembly including a relatively rigid proximal tube connected to a relatively flexible distal tube. With this construction, the flexible distal tube conforms with a curved shape defined by the introducer, and completes the irrigation channel.

Other aspects in accordance with principles of the present disclosure relate to a system for irrigating a frontal sinus target site of a patient. The system includes a surgical instrument and an irrigation source. The surgical instrument includes a handle, an elongate introducer, an irrigation channel, a nozzle, and an actuator assembly. The introducer rigidly projects from the handle and defines a relatively linear proximal segment and a relatively curved distal segment in longitudinal extension. The irrigation channel extends through the introducer, with the nozzle being fluidly coupled to the irrigation channel and rotatably maintained at a distal end of the introducer. The actuator assembly includes an actuator maintained by the handle and operable to effectuate rotation of the nozzle relative to the introducer. Finally, the irrigation source is fluidly connected to the irrigation channel. In some embodiments, the irrigation source includes a pump for delivering pressurized irrigant to the irrigation channel. In other embodiments, the irrigation source includes a liquid such as a surfactant, a gel, an antimicrobial agent, a steroid, or a growth hormone.

Yet other aspects in accordance with principles of the present disclosure relate to a method of irrigating a frontal sinus target site of a human patient. The method includes providing a surgical system as described above. The distal segment of the introducer is surgically inserted into the patient, with the nozzle being positioned within the frontal sinus of the patient. A pressurized flow of irrigant is dispensed from the nozzle toward a target site surface of the frontal sinus. In this regard, the nozzle is rotated relative to the outer tube while the pressurized flow is dispensed. In some embodiments, the method includes mechanically removing a substantial portion of the layer of biofilm from the target site surface via the dispensed, pressurized flow of irrigant.

BRIEF DESCRIPTION OF THE DRAWINGS

FIG. 1A is a schematic illustration of a frontal sinus irrigation system in accordance with principles of the present disclosure;

DETAILED DESCRIPTION

Figure 1B:
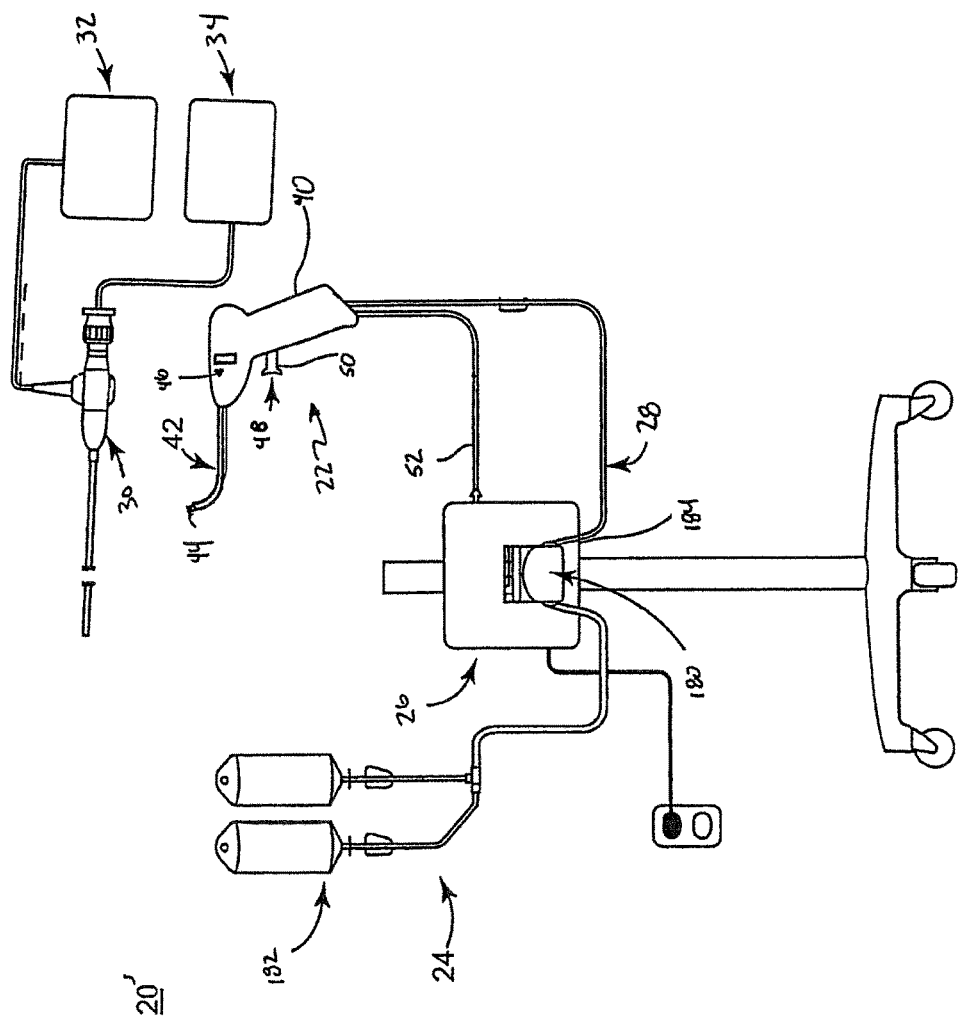
FIG. 1B is a schematic illustration of another frontal sinus irrigation system in accordance with principles of the present disclosure.

Aspects of environments described herein relate to systems, methods, and instruments for irrigating a frontal sinus region of a patient. In some instances, aspects of the present disclosure are useful for one or more of reducing, removing, or preventing growth of bacterial biofilms.

With the above in mind, FIG. 1A shows a surgical frontal sinus irrigation system 20 according to some embodiments and useful, for example, in removing bacterial biofilm. The system 20 includes a surgical irrigation instrument 22, an irrigation source 24, and a controller 26. In general terms, the irrigation source 24 provides fluid, or irrigant, to the instrument 22, for example via a delivery conduit 28 (e.g., tubing). The controller 26 controls aspects of operation of the system 20, and is indicated as being generally associated with the instrument 22 and the irrigation source 24.

The system 20 can include additional components. For example, another frontal sinus irrigation system 20' is shown in FIG. 1B and includes the same components as the system 20 (FIG. 1A), along with an optional endoscopic system including an endoscope 30 and related components such as a light source 32 and an imaging device 34. In general terms, the endoscope 30 can be of a conventional construction, with the light source 32 and the imaging device 34 facilitating visualization of a surgical area accessed by the surgical instrument 22 as described below. In other embodiments, however, the endoscope 30 and related components 32, 34 can be provided separately or apart from the system 20' and/or eliminated (such as with the system 20 of FIG. 1A).

The surgical irrigation instrument 22 can assume a variety of forms as described in greater detail below. In general terms, however, the instrument 22 includes a handle 40, an introducer 42, a nozzle 44, and an actuator assembly 46 (referenced generally). The introducer 42 extends from the handle 40 and is sized for surgical insertion into a frontal sinus region of a patient in a minimally invasive manner. The introducer 42 maintains the nozzle 44 (referenced generally) at a distal end thereof, as well as an irrigation channel (hidden in FIGS. 1A and 1B) that otherwise establishes a fluid connection between the nozzle 44 and the delivery conduit 28. The nozzle 44 is rotatably maintained by the introducer 42, with the actuator assembly 46 effectuating user control over a rotational position of the nozzle 44. Further, the handle 40 maintains an optional trigger assembly 48 (referenced generally) that includes a trigger 50. Upon depression of the trigger 50, a signal is delivered to the controller 26 via a connector 52 to prompt delivery of irrigant to the instrument 22. Alternatively, a component apart from the instrument 22 (e.g., a foot switch) can be included with the system 20, 20' for initiating irrigant delivery.

Figure 2:
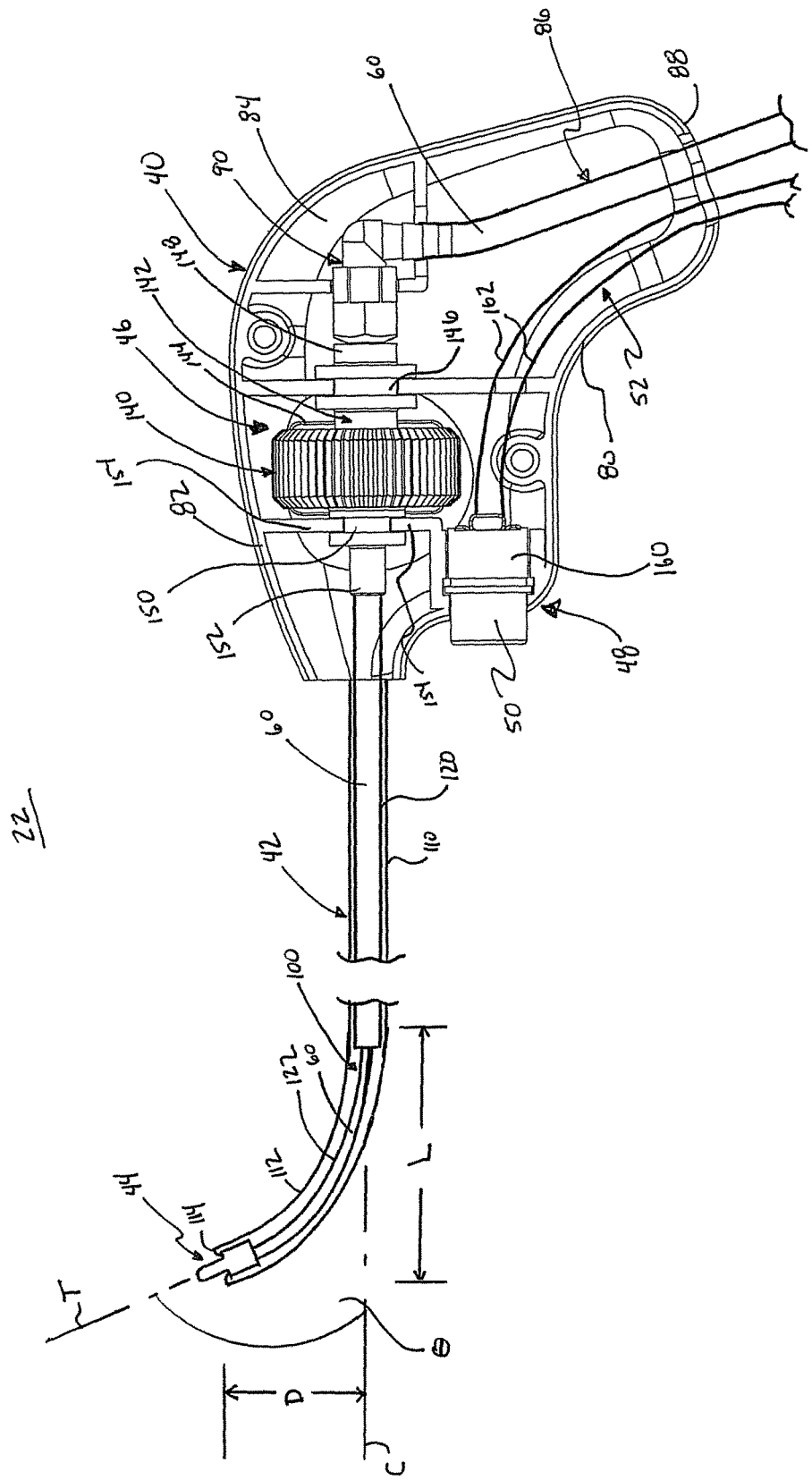
FIG. 2 is a side view of an irrigation instrument, with portions removed, in accordance with principles of the present disclosure and useful with the systems of FIGS. 1A and 1B.

One configuration of the surgical instrument 22 in accordance with the present disclosure is shown in greater detail in FIG. 2. A portion of the handle 40 has been removed in the view of FIG. 2 to better illustrate internal components of the instrument 22. Further, an irrigation channel 60 formed by the instrument 22 that extends through the introducer 42 is generally identified. Details on the various components are provided below. In general terms, however, the handle 40 maintains the introducer 42 that is otherwise adapted for minimally invasive delivery to a frontal sinus target site. In this regard, the introducer 42 rotatably maintains the nozzle 44 at a distal end thereof and through which pressurized flow of irrigant (not shown) is delivered, for example in performing a biofilm removal procedure. With this in mind, the actuator assembly 46 is operable by a user to effectuate rotation of the nozzle 44 relative to the introducer 42.

The handle 40 can assume a variety of forms, and generally serves as a housing for various components of the instrument 22, and retains the introducer 42. In some embodiments, the handle 40 has a pistol grip-like shape, defining a grip portion 80 and a nose 82. The grip portion 80 is sized and shaped for grasping by a user's hand, whereas the nose 82 is adapted for connection to the introducer 42. Alternatively, other configurations are also acceptable (e.g., the handle 40 can assume other shapes and/or sizes differing from the pistol grip-like design illustrated).

The handle 40 defines an interior 84 within which various components are housed. For example, the handle 40 can maintain irrigation tubing 86. The irrigation tubing 86 extends from a trailing end 88 of the handle 40, and is directed toward the nose 82 and thus the introducer 42. In this regard, the irrigation tubing 86 can be provided as a continuation of the delivery conduit 28 shown in FIG. 1A. Alternatively, the handle 40 can form or maintain a port configured to provide a fluid connection between the irrigation tubing 86 and the delivery conduit 28. Regardless, the irrigation tubing 86 serves to direct irrigation fluid from the irrigation source 24 (FIG. 1A) to the introducer 42.

In some embodiments, the irrigation tubing 86 terminates at a fitting 90 that is otherwise connected the actuator assembly 46 as described below. In this regard, an irrigation assembly 100 (described below) extends from an opposite side of the actuator assembly 46, with the fitting 90 establishing at least a portion of a fluid connection between the irrigation tubing 86 and the irrigation assembly 100. With this configuration, then, the irrigation assembly 100 extends into and through the introducer 42, and is fluidly connected to the nozzle 44. The irrigation tubing 86, the fitting 90, and the irrigation assembly 100 collectively form the irrigation channel 60 through which irrigation fluid is delivered from the irrigation source 24 (FIG. 1A) to the nozzle 44 as part of a frontal sinus irrigation procedure. Alternatively, a variety of other configurations for the irrigation channel 60 are also acceptable. For example, the irrigation channel 60 can be defined by a homogeneous body (e.g., the irrigation tubing 86) extending directly through the handle 40 and the introducer 42.

The introducer 42 has a generally elongated shape and is sized for minimally invasive insertion into the frontal sinus of a patient via the nasal passageway, extending from the nose 82 of the handle 40. In this regard, the introducer 42 maintains the irrigation channel 60 described above along a length thereof, and defines a proximal segment 110 and a distal segment 112. The proximal segment 110 extends from the nose 82, whereas the distal segment 112 extends from the proximal segment 110, terminating at a distal end 114. With this in mind, the introducer 42 is characterized as being rigid (e.g., will not elastically deform in response to a manually-applied bending force). Regardless, the nozzle 44 is maintained by the introducer 42 at the distal end 114.

As reflected in FIG. 2, relative to a longitudinal extension of the introducer 42 from the handle 40, the proximal segment 110 is relatively linear (within 5% of a linear shape), whereas the distal segment 112 is relatively curved (as compared to the relatively linear nature of the proximal segment 110). For example, with some configurations, the distal segment 112 defines an upwardly-extending curvature (relative to the orientation of FIG. 2) in extension from the proximal segment 110, such that the distal end 114 is positioned vertically above the proximal segment 110 (relative to, for example, the trailing end 88 of the handle 40). Stated otherwise, the proximal segment 110 forms a linear central axis C; the distal end 114 is offset from the central axis C by a distance D as identified in FIG. 2. Further, a bend angle θ is established between the central axis C (as defined by the linear proximal segment 110) and a central axis T of the introducer 42 at the distal end 114. With this construction, the curvature or bend angle θ associated with the distal segment 112 is commensurate with the normal anatomical curvature or shape of an adult human nasal/passageway frontal sinus whereby the distal end 114 is readily delivered through a patient's nasal opening (i.e., naris) and to the corresponding frontal sinus region with minimal articulation of the instrument 22 by a user. For example, in some embodiments, the distal segment 112 defines the bend angle θ to be in the range of 5°-100°, and in some embodiments in the range of 65°-85°. The distal end 114 is positioned vertically above the central axis C of the proximal segment 110 by the distance D in the range of 0.1-2.0 inches (2.5-51 mm), and some embodiments in the range of 0.75-1.25 inches. As a point of reference, it has surprisingly been found that forming the curved distal segment 112 in accordance with these dimensional parameters to have a working length L in the range of 0.354-0.748 inch (9-19 mm) can optimize performance of frontal nasal procedures. Along these same lines, an outer diameter or major dimension of the introducer 42 along at least the distal segment 112 is conducive to the above insertion techniques, and is not greater than 0.236 inch (6 mm), and in some embodiments in the range of 0.085-0.105 inch (2.2-2.7 mm).

The proximal segment 110 can have a variety of lengths (i.e., length of linear extension from the handle 40) appropriate for performing a desired procedure.

In some embodiments, the rigid nature of the introducer 42 is accomplished by forming the introducer 42 as a homogeneous tube or sleeve from a rigid, surgically-safe material such as surgical stainless steel, plastic, etc. Alternatively, the introducer 42 can consist of two or more discrete parts assembled to one another. Further, the introducer 42 can include one or more features that facilitate rotatable assembly of the nozzle 44 to the distal end 114. For example, with embodiments in which the introducer 42 is formed as an outer tube or sleeve, the distal end 114 can be rolled to define an inner diameter generally corresponding with a dimension of the nozzle 44 whereby the nozzle 44 is rotatably captured at the distal end 114. With this but one acceptable approach, the rolled distal end 114 serves to retain the nozzle 44 relative to the introducer 42 in the event the nozzle 44 is accidentally dislodged. Under these circumstances, then, the nozzle 44 will not migrate away from the introducer 42 into the patient. Alternatively, the introducer 42 can include additional components (e.g., bearing surfaces) that promote rotatable mounting of the nozzle 44.

As described above, in some embodiments, the irrigation channel 60 is defined, at least in part, by the irrigation assembly 100 that otherwise extends through the introducer 42. In this regard, the irrigation assembly 100 is configured to conform with the curvature(s) defined by the introducer 42, as well as to rotate the nozzle 44 via operation of the actuator assembly 46. With this in mind, the irrigation assembly 100 of FIG. 2 includes a proximal tube 120 and a distal tube 122. The proximal tube 120 extends from the actuator assembly 46 and is relatively rigid and linear. For example, in some embodiments, the proximal tube 120 is formed of steel and is akin to a hypodermic needle. Conversely, the distal tube 122 is attached to the proximal tube 120 and is flexible. More particularly, the distal tube 122 exhibits sufficient flexibility so as to readily assume the curved shape dictated by the distal segment 112 of the introducer 42. Thus, for example, the distal tube 122 can be provided as a thermoplastic flex tubing. Other configurations, such as a spiral cut metal tube, are also acceptable. The nozzle 44 is affixed to the distal tube 122 opposite the proximal tube 120, with the irrigation assembly 100 having a continuous lumen or other passageway that is fluidly connected to the nozzle 44. In other embodiments, the irrigation assembly 100 can include additional tube-like components; in yet other embodiments, the irrigation assembly 100 includes a single tube. Regardless, upon final assembly, the irrigation assembly 100 conforms with the linear and curved shapes defined by the introducer 42, and establishes a fluid connection of the nozzle 44 to the irrigation channel 60.

The nozzle 44 can assume a variety of forms, but in some configurations is adapted to generate a fan-like spray pattern, and is rotatably maintained by or assembled to, the distal end 114 of the introducer 42. As a point of reference, in accordance with some aspects of the present disclosure, the surgical irrigation instrument 22 is utilized to mechanically disrupt biofilms with a fluid stream as produced through the nozzle 44. With the one configuration of FIG. 3, the nozzle 44 is a fan spray-type nozzle that produces mechanical disruption on a "line" of tissue. When the nozzle 44 is rotated about its axis (as described below), this line can then sweep out a comparatively large area of tissue. Alternatively, the nozzle 44 can be an orifice-type nozzle.

Figure 3:
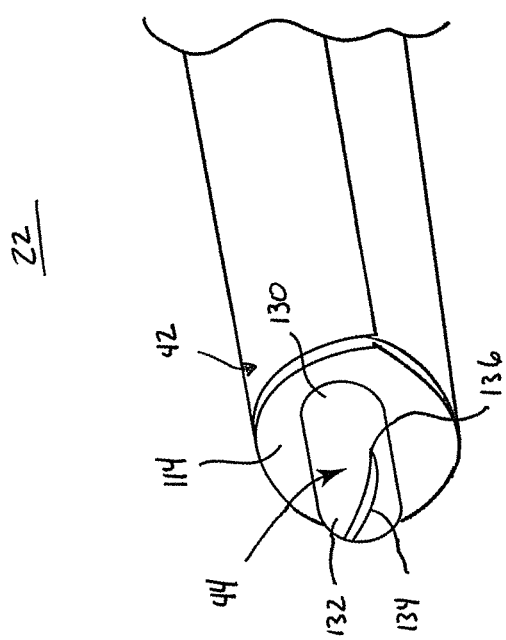
FIG. 3 is an enlarge, perspective view of a distal portion of the instrument of FIG. 2.

With the above in mind, the nozzle 44 can be a tubular-type body defining a base end 130 assembled to the introducer 42, and an opposite, leading, hemispherical end 132 at which a V-cut 134 is made. In some embodiments, and as shown in FIG. 3, the V-cut 134 is formed to extend along a side 136 of the nozzle 44 so as to produce a side-looking spray pattern (and thus cover more area with rotation of the nozzle 44 as described below). Alternatively, the V-cut 134 can be centrally formed relative to an axis of the nozzle 44. Regardless, it has been found that parameters that control the shape of the fan spray pattern generated by the nozzle 44 are the angle of the V-cut 134 and an inner diameter of the nozzle 44 orifice (not shown). With these parameters in mind, it has surprisingly been found that a nozzle configuration adapted to operate upon a supply flow rate of 6 mL/sec in generating a spray force equivalent to the force found with a 0.03 inch orifice nozzle at distances up to 1.3 inches can be achieved where the V-cut 134 defines an included angle in the range of 25°-100° and an inner diameter opening size in the range of 0.0001-0.0007 $inch^2$. Alternatively, however, a wide variety of other configurations for the nozzle 44 are also acceptable. Regardless, the nozzle 44 is assembled to the introducer 42. Thus, the leading end 132 of the nozzle 44 projects distally beyond the distal end 114 of the introducer 42 such that the spray pattern generated by or through the V-cut 134 is not impacted by the introducer 42.

Returning to FIG. 2, the actuator assembly 46 is configured to provide user-controlled movement or rotation of the nozzle 44 relative to the introducer 42 and includes, in some embodiments, an actuator 140 and a fluid coupling 142. The actuator 140 can be a control wheel that is rotatably maintained by the handle 40 such that at least a segment of the control wheel/actuator 140 is exteriorly exposed regardless of a rotational position. Thus, for example, the handle 40 forms an aperture 144 (partially hidden in FIG. 2) through which the actuator 140 partially projects. The actuator/control wheel 140 is located relative to the handle 40 such that a user can readily interface with the actuator/control wheel 140 when holding the handle 40 (e.g., at the grip portion 80).

The fluid coupling 142 is mounted to the actuator 140, and forms an internal passageway (not shown). With this but one acceptable arrangement of FIG. 2, the fluid coupling 142 is a rigid tubular body (e.g., metal) and further defines a first bearing feature 146 adjacent a first end 148, and a second bearing feature 150 adjacent a second end 152. The bearing features 146, 150 are configured for mating with corresponding surfaces (e.g., ribs 154) of the handle 40 such that the fluid coupling 142 is rotatably maintained relative to the handle 40. The fluid coupling 142 is affixed to the control wheel 140, and thus rotates with rotation of the control wheel 140 (and vice-versa). The first end 148 is configured for fluid attachment to the fitting 90, whereas the second end 152 is configured for fluid attachment to the irrigation assembly 100 (and in particular, the proximal tube 120 with the one embodiment of FIG. 2). In this regard, the fluid coupling 142 is rotatably assembled to the fitting 90, whereas a permanent fixation between the fluid coupling 142 and the proximal tube 120 is provided.

Upon final assembly, the internal passageway of the fluid coupling 142 forms a portion of the irrigation channel 60 that further includes the irrigation tubing 86, the fitting 90, and the irrigation assembly 100. Thus, irrigant flows along the irrigation channel 60 from the irrigation tubing 86 to the nozzle 44. Further, rotation of the control wheel 140 is transferred to the fluid coupling 142. Rotation of the fluid coupling 142, in turn, is transferred to the irrigation assembly 100 and thus the nozzle 44 (it being understood that the coupling 142 will rotate relative to the fitting 90, for example where the fitting 90 is a swivel fitting). With some constructions, the control wheel 140, and thus the nozzle 44, is rotatable in two directions (i.e., clockwise and counter-clockwise), with the nozzle 44 being articulable through a full 360 degrees of rotation.

The above description of the actuator assembly 46 is but one acceptable design for effectuating user-controlled rotation of the nozzle 44. Thus, the control wheel 140/coupling 142 can be replaced by or include other components. For example, the actuator 140 can be a sliding-type mechanism. Where the actuator 140 is provided as a control wheel, however, indicia (not shown) can be provided along the control wheel 140 that is viewable external the handle 40, and provides a user with a visual indication of a rotational position of a nozzle 44 relative to the introducer 42, and in particular the line-type spray pattern produced thereby. Alternatively, the indicia can be eliminated.

Finally, the surgical irrigation instrument 22 can further include the optional trigger assembly 48. With these embodiments, the trigger assembly 48 is maintained by the handle 40 and includes the activation member or trigger 50, a sensor 160 (drawn generally), and the connector 52. The trigger 50 extends externally from the grip portion 80 and is adapted to be actuated by a user (not shown), for example, via a sliding interface relative to the grip portion 80. In this regard, the trigger assembly 48 can further include other components (not shown) that serve to bias the trigger 50 to the extended position (relative to the grip portion 80) reflected in FIG. 2. Actuation of the trigger 50 thus entails a pushing force being applied thereon, sufficient to overcome a force of the biasing device to thereby slide the trigger 50 inwardly; alternatively, other actuation arrangements are also acceptable. The sensor 160 is adapted to provide an output indicative of actuation (e.g., sliding movement) of the trigger 50 and thus can assume a variety of forms appropriate for sensing movement of the trigger 50. The connector 52, in turn, is adapted to carry, or transmit, the output from the sensor 160. Thus, the connector 52 can assume a variety of forms (e.g., wiring 162 as shown, tubing, etc.), and is connected (wired or wireless) to the controller 26 as shown in FIG. 1A. For example, the connector 52 is electronically connected to the sensor 160, and projects externally from the handle 40 via the trailing end 88. In other embodiments, the trigger assembly 48 can be a simple, electrical switch, with the connector wires 162 transmitting an output from the switch to the controller 26. In yet other configurations, the trigger assembly 48 can be eliminated (e.g., a separate control switch is provided apart from the surgical irrigation instrument 22).

With the above explanations in mind, upon final assembly, the surgical irrigation instrument 22 is constructed to deliver a focused, pressurized spray or flow of fluid from the distal end 114 of the introducer 42 via the nozzle 44. In this regard, the supply of irrigation fluid is provided via the irrigation tubing 86/irrigation channel 60. The spatial, angular orientation of the distal end 114, and thus of the nozzle 44, relative to the handle 40 is rigidly maintained by the introducer 42. Conversely, a spatial orientation of the line spray pattern generated by the nozzle 44 can be "rotated" by a user via the actuator assembly 46 (and in particular by manipulation of the actuator/control wheel 140).

Returning to FIG. 1A, regardless of an exact construction of the surgical irrigation instrument 22 (e.g., the instrument 22 of FIG. 2 or other surgical irrigation instrument configuration envisioned by the pending disclosure), other components of the system 20 can assume a variety of forms. For example, the irrigation source 24 can include a pump 180 connected to a reservoir 182. In some embodiments, the pump 180 is a peristaltic pump, such as those typically used in association with surgical and/or endoscopic procedures, with the pump 180 serving to pressurize a flow of fluid from the reservoir 182 to the instrument 22 as described below. The reservoir 182 can include one or more IV bags, for example, filled with an irrigant, including the irrigating fluids described in U.S. patent application Ser. No. 11/431,495 entitled "Biofilm Extracellular Polysaccharide Solvating (EPS) System," filed May 10, 2006 and an entirety of the teachings of which are incorporated herein by reference. In some embodiments, the irrigant includes medicaments, including those adapted to interfere with bacterial biofilm regrowth, surfactants, gels, antimicrobials, steroids, growth hormones, chemicals for reducing biofilm adhesion force, and others. Other irrigants, such as water or saline, can also be employed.

The irrigation source 24 is connected to the instrument 22 via the delivery conduit 28, which is in some embodiments a tubing set. For example, the delivery conduit 28 can be in fluid communication with (as formed as part of) the irrigation tubing 86 (FIG. 2) such as by a port (not shown) that, in turn, is in fluid communication with the nozzle 44 as previously described. Further, the delivery conduit 28 can include an auxiliary inlet or port (not shown) for introducing medicaments into irrigant (not shown) flowing from the irrigation source 24 or reservoir 182, for example medicaments such as those previously referenced.

The controller 26 controls operation of the system 20 and is designed as being physically associated with the irrigation source 24, although the controller 26 is optionally a stand-alone device or physically associated with any of the other system components including, for example, the connector 52 provided with the instrument 22. The controller 26 can assume a variety of forms capable of performing various functions and can include a microchip, a memory, and/or other appropriate control electronics.

The controller 26 is placed in communication with the instrument 22 and the irrigation source 24, and includes a housing 184. For example, the controller 26 can be electronically connected to the trigger assembly 48 of the instrument 22 via the connector 52. The controller 26 can also be placed in direct or indirect communication with the irrigation source 24, such as by controlling operations of the pump 180. Along these lines, the controller 26 can be programmed or adapted to operate the system 20 according to a variety of desired irrigation profiles, including ramp actuation, time delays, varied flow patterns, and others.

Figure 4:
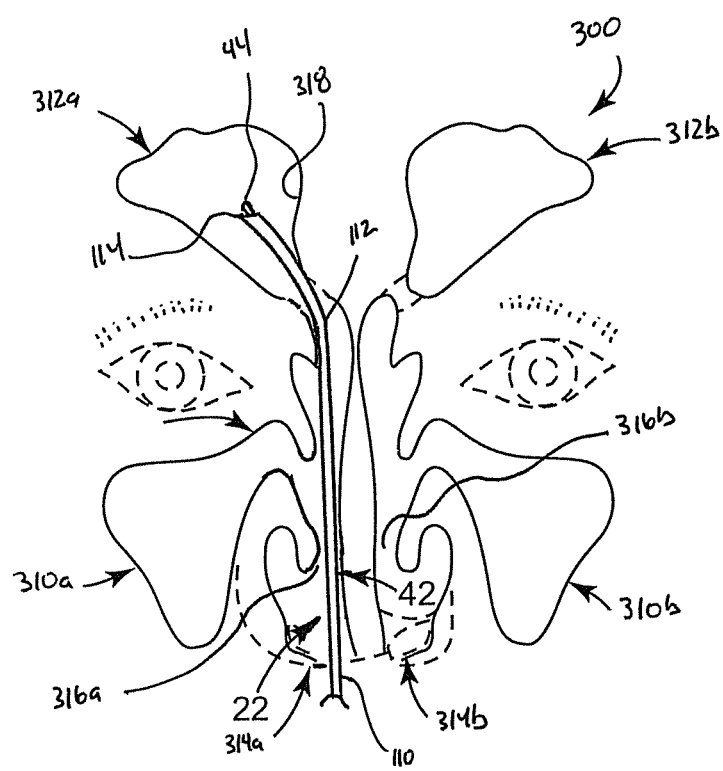
FIG. 4 illustrates methods of irrigating a frontal sinus relative to a human anatomy in accordance with the present disclosure

During use, the surgical irrigation system 20 (or 20') can be employed to perform a variety of procedures at a frontal sinus location of the patient. By way of but one example, FIG. 4 illustrates internal bodily structures 300 of a patient, including sinus cavities such as the maxillary sinuses 310a, 310b and frontal sinuses 312a, 312b that are accessed through respective naris 314a, 314b and their corresponding nasal passageways 316a, 316b. It should be noted that external features of the patient, including the nares 314a, 314b, are shown in dashed lines.

With the above anatomy in mind, the system 20, 20' can be employed to perform various irrigation-related procedures in one more both of the frontal sinuses 312a and/or 312b, for example to remove a layer of biofilm. For example, a target site 318 is reflected in FIG. 4 as existing within the first frontal sinus 312a. In accordance with but one example procedure, the target site 318 is ciliated epithelium of the frontal sinus 312a that has an associated layer of bacteria and corresponding biofilm (not shown). In other techniques, the target site 318 is an artificial structure (not shown), such as sinus packing or a stent covered with a layer of bacterial biofilm, for example.

With combined reference to FIGS. 2 and 4, and with the foregoing description of the system 20 in mind, some methods of irrigating the frontal sinus 312a, for example in removing bacterial biofilm (not shown) from the target site 318 (or any other target site within one or both of the frontal sinuses 312a, 312b), includes delivering the distal end 114 of the introducer 42, and thus the nozzle 44, through the naris 314a that corresponds with the frontal sinus 312a to be treated. In particular, the distal end 114/nozzle 44 is inserted through the naris 314a and into the frontal sinus 312a via the nasal passageway 316a. In this regard, the relatively small outer diameter of the distal segment 112 of the introducer 42 minimizes possible tissue trauma as part of this insertion. Further, the curvature of the distal segment 112 and the overall length of the introducer 42 allows the caregiver to relatively easily direct the distal end 114/nozzle 44 into the frontal sinus 312a with minimal hand manipulations of the handle 40. For example, while grasping the handle 40, the user simply lifts or tilts the handle 40 upwardly, with the rigid introducer 42 transferring this motion directly to the distal end 114/nozzle 44 to effectuate sliding through the nasal passageway 316a. Thus, the instrument 22 is ergonomically conducive to minimally invasive, frontal sinus procedures.

In some embodiments, and with additional reference to FIG. 1B, the endoscope 30 and related components 32, 34 are provided and are employed in properly positioning the introducer 42/nozzle 44 relative to the target site 318. Along these same lines, a functional endoscopic sinus surgery (FESS) may also be performed prior to, or concurrently with, insertion of the introducer 42. For example, the endoscope 30 and/or the instrument 22 is optionally adapted for, and/or used in combination with, other implements as desired for gaining access to the target site 318 as part of an FESS procedure.

Once the nozzle 44 is positioned relative to the target site 318 as desired, the user (not shown) then prompts delivery of a pressurized flow of irrigant to the target site 318, for example to effectuate removal or eradication of a substantial amount of the bacterial biofilm (not shown) from the target site 318, via operation of the trigger assembly 48. In response, a signal is sent to the controller 26 that in turn prompts activation of the irrigation source 24 (e.g., the pump 180) to provide a flow of irrigant through the irrigation channel 60 described above and thus to the nozzle 44. It is contemplated that the flow of irrigant will be directed through the nozzle 44 at a variety of flow rates according to various embodiments, including a flow rate from about 2 mL/sec to about 12 mL/sec. In some embodiments, the system 20/20' is adapted to cause pulse flow through the nozzle 44, and in others substantially continuous flow, and in still others, a flow pattern other than pulsed or substantially continuous flow.

The flow of irrigant dispensed from the nozzle 44 directly impinges upon, or otherwise directly strikes the target site 318 to irrigate the target site 318. For example, with biofilm removal procedures, the dispensed flow of irrigant mechanically agitates or disrupts and removes a substantial portion of, or substantially all of, the biofilm (not shown). In this regard, it should be noted that the pressure and/or flow rate of the irrigant is selected to promote mechanical removal of the biofilm without substantial damage to underlying tissue, such as a ciliated epithelium layer. For example, a pressure of less than about 50 psi can be selected, although other pressures are also acceptable.

With continued flow of the pressurized irrigant from the nozzle 44, the user optionally periodically and/or continuously rotates the nozzle 44 via the actuator assembly 46. As previously described, in some embodiments, the nozzle 44 generates a line, fan spray pattern; with rotation of the nozzle 44, then, a path is effectively "swept" at or across the target site 318, such that the introducer 42 can remain relatively stationary while treating a relatively large area. With this approach, the ability to accurately locate the nozzle 44 relative to the target site 318 is of less concern in that a relatively large surface area can be acted upon by the pressurized irrigant delivered from the nozzle 44. In fact, in some embodiments, the relatively large treatment area reduces the need for an endoscope having complicated optics, and can in fact eliminate the need for use of a dedicated endoscope with the instrument 22. Alternatively, however, the nozzle 44 can assume a wide variety of other configurations and/or the ability to rotate the nozzle 44 relative to the introducer 42 need not be provided.

As a point of reference, with frontal sinus irrigation procedures, the frontal sinus is effectively an open system in that irrigant delivered into the frontal sinus will naturally drain out. Thus, the irrigation system 20/20' need not provide forced aspiration from the target site 318. However, suction or aspiration features or components can be incorporated where necessary/desired.

The delivery of irrigant from the nozzle 44 can continue for as long as deemed necessary by the user. Where desired, other irrigants can subsequently be delivered to the frontal sinus target site 318 prior to removal of the distal end 114/nozzle 44, such as in administering one or more of the medicaments described above. Where the user desires to stop (and/or reduce) the flow of irrigant, the trigger assembly 48 (or other external device) can simply be released.

The systems, instruments, and methods of the present disclosure provide a marked improvement over previous techniques and devices used to treat various ailments in which frontal sinus irrigation is required. In this regard, the irrigation instrument is uniquely configured for simplified accessing of the frontal sinus, and provides for a relatively large area of irrigation coverage. With embodiments in which the instrument is used in removing bacterial biofilm, by effectuating biofilm eradication using a focused, pressurized fluid, a more complete treatment is provided to the patient on a minimally invasive basis. Further, with sinus applications, a drainage pathway(s) is restored, ventilation of the treatment site is provided (thus minimizing opportunities for biofilm regrowth), and other functional and endoscopic sinus surgery treatments can be provided (e.g., topical application of medicaments, etc.).

Although the present disclosure has been described with reference to preferred embodiments, workers skilled in the art will recognize that changes can be made in form and detail without departing from the spirit and scope of the present disclosure. For example, the systems and instruments of the present disclosure can be used in performing frontal sinus irrigation procedures apart from bacterial biofilm removal. Further, the systems and instruments can be employed in a variety of settings including operating room and caregiver office settings.

What is claimed is:

1. A surgical instrument for irrigating a frontal sinus target site of a patient, the instrument comprising:
    a handle;
    an elongate introducer extending from the handle and defining a proximal segment and a distal segment terminating at a distal end, the introducer rigidly forming at least a portion of the proximal segment to be relatively linear and at least a portion of the distal segment to be relatively curved as compared to the relatively linear portion in longitudinal extension of the introducer from the handle, a rigidity of the relatively linear portion and the relatively curved portion characterized by each portion not elastically deforming in response to a manually applied bending force;
    an irrigation channel comprising a tubular body extending through the introducer, the tubular body having a terminal first end, the first end disposed within the introducer adjacent to the distal end;
    a nozzle fluidly connected to the irrigation channel at the first end of the tubular body, the nozzle is maintained partially within and rotatably assembled to the distal end of the introducer such that the nozzle is rotatable relative to the introducer; and
    an actuator assembly including an actuator maintained by the handle and connected to the nozzle; wherein the instrument is configured such that movement of the actuator causes the nozzle to rotate relative to the introducer.

2. The instrument of claim 1, further comprising: an irrigation assembly extending within the introducer, the irrigation assembly forming a portion of the irrigation channel.

3. The instrument of claim 2, wherein the irrigation assembly includes:
    a proximal tube; and a distal tube extending from the proximal tube;
    wherein the distal tube has a flexibility greater than a flexibility of the proximal tube and assumes a curvature defined by the introducer.

4. The instrument of claim 3, wherein the proximal tube is relatively rigid.

5. The instrument of claim 2, wherein the irrigation assembly mechanically couples the nozzle and the actuator assembly.

6. The surgical instrument of claim 2, wherein the irrigation assembly includes a distal tube and a proximal tube; wherein a first diameter of the distal tube is less than a second diameter of the proximal tube.

7. The instrument of claim 1, wherein the nozzle is configured to generate a fan-type spray pattern.

8. The instrument of claim 1, wherein the nozzle is rotatable relative to the introducer through 360 degrees of rotation.

9. The instrument of claim 1, wherein the actuator assembly includes:
    a wheel rotatably secured to the handle;
    a first coupling attached to the wheel and rotatably maintained within the handle;
    wherein the first coupling is connected to the nozzle;
    a second coupling fluidly connected to the first coupling, the second coupling being affixed relative to the handle and rotatably associated with the first coupling such that fluid connection between the first and second couplings remains intact with rotation of the wheel; and
    irrigation tubing connected to the second coupling and extending from the handle.

10. The instrument of claim 1, further comprising:
    an electrical switch assembly adapted to prompt activation of an external pump, the switch assembly including:
    a switch mechanism maintained by the handle; and
    wiring electrically connected to the switch mechanism and extending from the handle.

11. The instrument of claim 1, wherein the relatively curved portion of the distal segment of the introducer has a working length on an order of 9-19 mm.

12. The instrument of claim 1, wherein the relatively curved portion of the distal segment defines a bend angle in a range of 65°-85°.

13. A system for irrigating a frontal sinus target site of a human patient, the system comprising:
    a surgical irrigation instrument comprising:
        a handle,
        an elongate introducer extending from the handle and defining a proximal segment and a distal segment terminating at a distal end, the introducer rigidly forming at least a portion of the proximal segment to be relatively linear and at least a portion of the distal segment to be relatively curved as compared to the relatively linear portion in longitudinal extension of the introducer from the handle, a rigidity of the relatively linear portion and the relatively curved portion characterized by each portion not elastically deforming in response to a manually applied bending force, an irrigation channel comprising a tubular body extending through the introducer, the tubular body having a terminal first end disposed adjacent the distal end of the introducer, a nozzle fluidly connected to the irrigation channel at the first end of the tubular body and rotatably extending within and retained by the distal end of the introducer such that the nozzle is rotatable relative to the introducer, the distal end defining an inner diameter to rotatably capture the nozzle, and an actuator assembly including an actuator maintained by the handle and connected to the nozzle, wherein the instrument is configured such that movement of the actuator causes the nozzle to rotate relative to the introducer; and an irrigation source fluidly connected to the irrigation channel.

14. The system of claim 13, further comprising:
an irrigation assembly disposed within the introducer, the irrigation assembly forming a portion of the irrigation channel.

15. The system of claim 14, wherein the irrigation assembly includes a distal tube and a proximal tube; wherein a first diameter of the distal tube is less than a second diameter of the proximal tube.

16. The system of claim 13, wherein the irrigation source includes a pump for delivering a pressurized irrigant from a reservoir to the irrigation channel, the system being configured such that a pressurized flow of the irrigant is dispensed from the nozzle upon operation of the pump.

17. A method for irrigating a frontal sinus target site of a human patient, the method comprising:
providing a surgical irrigation instrument comprising:
a handle, an elongate introducer extending from the handle and defining a proximal segment and a distal segment terminating at a distal end, the introducer rigidly forming at least a portion of the proximal segment to be relatively linear and at least a portion of the distal segment to be relatively curved as compared to the relatively linear portion in longitudinal extension of the introducer from the handle, a rigidity of the relatively linear portion and the relatively curved portion characterized by each portion not elastically deforming in response to a manually applied bending force, an irrigation channel extending through the introducer, an irrigation assembly extending within the introducer and forming a portion of the irrigation channel, the irrigation assembly defining a proximal tube and a distal tube extending from the proximal tube, wherein the distal tube has a flexibility greater than a flexibility of the proximal tube and assumes a curvature defined by the introducer, a nozzle fluidly connected to the distal tube and rotatably maintained partially within the introducer at the distal end of the introducer, an actuator assembly including an actuator maintained by the handle and connected to the nozzle, wherein the instrument is configured such that movement of the actuator causes the nozzle to rotate relative to the introducer;

surgically inserting the distal segment of the introducer into a naris of the patient;

positioning the nozzle within a frontal sinus of the patient;

dispensing a pressurized flow of an irrigant from the nozzle toward a target site surface of the frontal sinus; and rotating the nozzle relative to the introducer while dispensing the pressurized flow.

18. The method of claim 17, wherein the target site surface includes a layer of bacterial biofilm, and further wherein dispensing the pressurized flow includes mechanically removing a substantial portion of the layer of biofilm from the target site surface.

19. The method of claim 17, further comprising applying a medicament to the target site through the nozzle, the medicament adapted to interfere with bacterial biofilm regrowth.

20. The method of claim 17, wherein surgically inserting the distal segment of the introducer includes the relatively curved portion of the distal segment forming a bend angle corresponding with a curvature from the naris to the frontal sinus of the patient.

\* \* \* \* \*